US006593369B2

(12) United States Patent
Neal

(10) Patent No.: US 6,593,369 B2
(45) Date of Patent: Jul. 15, 2003

(54) METHODS, COMPOSITIONS, AND KITS FOR ENHANCING FEMALE SEXUAL DESIRE AND RESPONSIVENESS

(75) Inventor: Gary W. Neal, Knoxville, TN (US)

(73) Assignee: Vivus, Inc., Mountain View, CA (US)

(*) Notice: Subject to any disclaimer, the term of this patent is extended or adjusted under 35 U.S.C. 154(b) by 5 days.

(21) Appl. No.: 09/880,188

(22) Filed: Jun. 12, 2001

(65) Prior Publication Data

US 2001/0044467 A1 Nov. 22, 2001

Related U.S. Application Data

(63) Continuation of application No. 09/391,412, filed on Sep. 8, 1999, which is a continuation-in-part of application No. 08/954,122, filed on Oct. 20, 1997, now abandoned.

(51) Int. Cl.[7] ........................ A61K 31/19; A61K 31/557
(52) U.S. Cl. ........................ 514/573; 514/874
(58) Field of Search ................................ 514/573, 874

(56) References Cited

U.S. PATENT DOCUMENTS

| 3,800,038 A | 3/1974 | Rudel |
| 4,128,577 A | 12/1978 | Nelson |
| 4,254,145 A | 3/1981 | Birnbaum |
| 4,454,339 A | 6/1984 | Skuballa et al. |
| 4,507,323 A | 3/1985 | Stern |
| 4,521,421 A | 6/1985 | Foreman |
| 4,680,312 A | 7/1987 | Johnson |
| 4,801,587 A | 1/1989 | Voss et al. |
| 4,818,517 A | 4/1989 | Kwee et al. |
| 4,961,931 A | 10/1990 | Wong |
| 4,976,692 A | 12/1990 | Atad |
| 5,190,967 A | 3/1993 | Riley |
| 5,242,391 A | 9/1993 | Place et al. |
| 5,474,535 A | 12/1995 | Place et al. |
| 5,565,466 A | 10/1996 | Gioco et al. |
| 5,576,290 A | 11/1996 | Hadley |
| 5,698,589 A | 12/1997 | Allen |
| 5,731,339 A | 3/1998 | Lowrey |
| 5,773,457 A | 6/1998 | Nahoum |
| 5,877,216 A | 3/1999 | Place et al. |
| 5,891,915 A | 4/1999 | Wysor et al. |

FOREIGN PATENT DOCUMENTS

| WO | WO 94/28902 | 12/1994 |
| WO | WO 96/16644 | 6/1996 |
| WO | WO 97/32572 | 9/1997 |
| WO | WO 99/20266 | 4/1999 |
| WO | WO 99/21562 | 5/1999 |

OTHER PUBLICATIONS

Akkus et al. (1995), "Duplex Ultrasonography After Prostaglandin E1 Injection of the Clitoris in a Case of Hyperreactio Luteinalis," *The Journal of Urology* 153:1237–1238.
Craig (1975), "Prostaglandins in Reproductive Physiology," *Postgraduate Medical Journal* 51:74–84.
Ensor et al. (1995), "15–Hydroxyprostaglandin Dehydrogenase," *J. Lipid Mediators Cell Signalling* 12:313–319.
Levin (1980), "The Physiology of Sexual Function," *Clinics in Obstetrics and Gynaecology* 7(2):213–252.
Roy et al. (1989) "Prostaglandin 15–Hydroxydehydrogenase Activity in Human Penile Corpora Cavernosa and its Significance in Prostaglandin–Mediated Penile Erection," *British Journal of Urology* 64:180–182.
Sarrel (1990), "Sexuality and Menopause," *Obstetrics and Gynecology* 75:(4):26S–30S.
Uekama et al. (1984), "Inclusion Complexation of Prostaglandin F2 Alpha With Gamma–Cyclodextrin in Solution and Solid Phases," *Journal of Pharmaceutical Sciences* 73(3)382–384.

*Primary Examiner*—Theodore J. Criares
(74) *Attorney, Agent, or Firm*—Dianne E. Reed; Reed & Eberle LLP

(57) ABSTRACT

Topical application of a prostaglandin directly to the clitoris is effective for enhancing female sexual desire and responsiveness.

15 Claims, No Drawings

METHODS, COMPOSITIONS, AND KITS FOR ENHANCING FEMALE SEXUAL DESIRE AND RESPONSIVENESS

CROSS-REFERENCE TO RELATED APPLICATIONS

This is a continuation of U.S. patent application Ser. No. 09/391,412, filed Sep. 8, 1999, which was a continuation-in-part of U.S. patent application Ser. No. 08/954,122, filed Oct. 20, 1997 now abandoned.

BACKGROUND OF THE INVENTION

1. Field of the Invention

The present invention relates to methods for enhancing female sexual desire and responsiveness. The present method also relates to compositions and kits useful for enhancing female sexual desire and responsiveness.

2. Discussion of the Background

The female sexual response cycle can be divided into the four following phases (as adapted from *Diagnostic and Statistical Manual IV*, "Sexual and Gender Identity Disorder," American Psychiatric Association, Washington, D.C., pp. 493–494 and 735–751, 1994:

1. Desire, which includes fantasies about sexual activity and the desire to have sexual activity;
2. Excitement, which consists of subjective senses of sexual pleasure and accompanying physiological changes including vasocongestion in the pelvis, vaginal lubrication, and expansion and swelling of the external genitalia;
3. Orgasm, which consists of peaking of sexual pleasure with release of sexual tension; and
4. Resolution, which consists of a sense of muscular relaxation and general well-being.

Disorders of female sexual desire or response are estimated to affect from 30 to 50 percent of the adult population in various studies (see, e.g., S. G. Nathon, "The Epidemiology of the DSM-III Psychosexual Dysfunctions," *J. of Sex and Marital Therapy*, vol. 12, no. 4, pp. 267–281 (1986); *Diagnostic and Statistical Manual IV*, "Sexual and Gender Identity Disorder," American Psychiatric Association, Washington, D.C., pp.493–539, 1994; M. Osborn et al, "Sexual dysfunction among middle aged women in the community," *British Medical Journal*, vol. 296, pp. 959–962 (1988); E. Frank et al, "Frequency of Sexual Dysfunction in "Normal Couples"," *New England Journal of Medicine*, vol. 299, pp. 111–115 (1978); and K. Garde et al, "Female sexual behavior: a study in a random sample of forty-year-Old Danish Women," *Maturitas*, vol. 2, pp. 225–240 (1980)). These very common disorders may have a variety of causes including psychogenic etiologies, anatomical disorders, drug-induced disorders, diabetes mellitus, post-surgical disorders, atherosclerosis, post-traumatic disorders, as well as endocrine etiologies.

The search for effective pharmacologic treatments to influence sexual behavior has been a preoccupation of all societies throughout history (see, e.g., E. L. Abel, *Psychoactive Drugs and Sex*, Plenum Press, New York, 1985; and J. Buffum, "Substance abuse and high-risk sexual behavior," *J. Psychoact. Drugs*, vol. 20, pp.165–168 (1988)). In one of the few scientific review articles on this topic (R. C. Rosen et al, "Prosexual Drugs: Empirical Status of the "new Aphrodisiacs"," *Archives of Sexual Behavior*, vol. 22(6), pp.521–543 (1993)), Rosen states: "In particular, the search for the perfect aphrodisiac—a drug that will heighten sexual desire, pleasure and performance has been a continuing cultural quest from ancient to modern times. Natural substances such as datura, belladonna and henbane were key ingredients in the sexual orgies of ancient fertility cults. Yohimbine has long been used by the natives of Africa to enhance their sexual prowess, as was the mandrake plant in medieval Europe (E. L. Abel, *Psychoactive Drugs and Sex*, Plenum Press, New York, 1985). Oysters, ginseng and Vitamin E have similarly been recommended at various times as possessing aphrodisiacal qualities (R. C. Rosen et al, *Sexuality*, Random House, New York, 1984). Given the perennial search for an effective aphrodisiac, it is surprising that relatively few drugs have been demonstrated to have specific prosexual properties."

L-dopa has been reported to stimulate sexual responsiveness in male and female patients. However, subsequent studies have yielded inconsistent or contradictory results regarding the effect of L-dopa on sexual behavior (M. Hyppa et al, "Is L-dopa an aphrodisiac in patients with Parkinson's disease?," in *Sexual Behavior Pharmacology and Biochemistry*, M. Sandler et al, Eds., Plenum Press, New York, 1975; and O. Benkert et al, "Effect of L-dopa on sexually impotent patients," *Psychopharmacologia*, vol. 23, pp. 91–95 (1972)). Most of these studies deal exclusively with men and extremely few studies have even mentioned women. Apomorphine has been investigated for erectile dysfunction in men, but there have been no positive reports in women. Nomifensine and bupropion which are atypical anti-depressants acting on dopamine have been reported to have stimulatory effects on females with decreased sexual desire (S. Lal et al, "Apomorphine induced penile tumescence in impotence patients—preliminary findings," *Prog. Neurol. Psychopharmacol. Biol. Psychiat.*, vol. 11, pp. 235–242 (1987). Subsequent studies by Klein et al did not replicate these effects (K. B. Klein et al, "Drug treatment of patients with inhibited sexual desire: A controlled clinical trial," presented at the SSTAR annual meeting, New Orleans, 1987).

Prostaglandins may have a possible role in human ovulation (G. M. Craig, "Prostaglandins in reproductive physiology," *PMJ*, vol. 51, pp. 74–84 (1975)). Prostaglandin $E_1$ (PGE-1), prostaglandin $E_2$ (PGE-2), and prostaglandin $F_{2\alpha}$ (PGF-2α) cause uterine contraction in women. Indeed, PGE-2 is presently used in the United States for inducing labor and cervical ripening.

Present therapies for disorders of sexual response and desire include various types of psychotherapeutic counseling (J. LoPiccolo et al, "Treatment of Sexual Dysfunction," *J. of Counseling and Clinical Psychology*, vol. 54(2), pp. 158–167 (1986)). There is also a report of using electrical stimulators placed inside the vagina to induce orgasms (see: D. Boutos, "Apparatus for stimulating penile, scrotal, anal, vaginal, and clitoral tissue," U.S. Pat. No. 5,571,118). Neither of these methods are particularly desirable or effective in treating these disorders.

Thus, there remains a need for a method for enhancing female sexual desire and responsiveness. There also remains a need for pharmaceutical compositions and kits useful for enhancing female desire and responsiveness.

SUMMARY OF THE INVENTION

Accordingly, it is one object of the present invention to provide novel methods for enhancing female sexual desire and responsiveness.

It is another object of the present invention to provide novel pharmaceutical compositions which are useful for enhancing female sexual desire and responsiveness.

It is another object of the present invention to provide novel kits useful for enhancing female sexual desire and responsiveness.

These and other objects, which will become apparent during the following detailed description, have been achieved by the inventor's discovery that application of a prostaglandin directly to the clitoris of a female is effective for enhancing female sexual desire and responsiveness.

DETAILED DESCRIPTION OF THE PREFERRED EMBODIMENTS

Thus, in a first embodiment, the present invention provides novel methods for enhancing female sexual desire and responsiveness. In the context of the present invention, the term enhancing female sexual desire and responsiveness includes the treatment of disorders of female sexual desire and/or response. The term disorders of female sexual desire and/or response means any disorder which causes a decrease in or absence of female sexual responsiveness or female sexual desire. This includes any persistent or recurrent deficiency or absence of sexual fantasies and desire for sexual activity. It also includes decreases in the physiological response to sexual stimulation such as slowed or decreased erectile response of the female erectile tissues; slowed, decreased or absent lubrication of the vagina; slowed, decreased, or absent ability to have orgasms; decreased intensity of or pleasure in orgasms; frigidity; sexual aversion; and disorders of female sexual desire and response that are secondary to a general medical condition such as the menopausal or post-menopausal state, radiotherapy of the pelvis, atheroscelerosis, pelvic trauma or surgery, peripheral neuropathies, autonomic neuropathies, diabetes mellitus, and disorders of the innervation of any of the sexual organs. This term also includes substance-induced sexual dysfunction including but not limited to decreases in desire and responsiveness secondary to anti-depressants, neuroleptics, anti-hypertensives, opiates, alcohol and any other drug found to decrease or eliminate any part of the sexual response cycle. Primary and secondary anorgasmia are included. Vaginismus (a psychologically induced spasm of the vagina) may be resistant to the present method and compositions.

Specifically, the present method involves application of a prostaglandin directly to the clitoris. Examples of suitable prostaglandins include PGE-1; PGE-2; PGF-2α; PGA-1; PGB-1; PGD-2; PGE-M; PGF-M; PGH-2; PGI-2; 19-hydroxy-PGA-1; 19-hydroxy-PGB-1; PGA-2; PGB-2; 19-hydroxy-PGA-2; 19-hydroxy-PGB-2; PGB-3; PGF-1α; 15-methyl-PGF-2α; 16,16-dimethyl-Δ$^2$-PGE-1 methyl ester; 15-deoxy-16-hydroxy-16-methyl-PGE-1 methyl ester; 16,16-dimethyl-PGE-2; 11-deoxy-15-methyl-PGE-1; 16-methyl-18,18,19,19-tetrahydrocarbacyclin; (16RS)-15-deoxy-16-hydroxy-16-methyl-PGE-1 methyl ester; (+)-4,5-didehydro-16-phenoxy-α-tetranor-PGE-2 methyl ester; 11-deoxy-11a, 16,16-trimethyl-PGE-2; (+)-11a, 16a,b-dihydroxy-1,9-dioxo-1-(hydroxymethyl)-16-methyl-trans-prostene; 9-chloro -16,16-dimethyl-PGE-2; arboprostil; and semisynthetic or synthetic derivatives of these natural prostaglandins, or any derivative or any prostaglandin analog capable of acting as a vasodilator or neuromodulator. Cyclodextrin complexes are also included as they may enhance the activity of the solution and stabilize the prostaglandin. Racemic, optically enriched or purified stereoisomers of any of these compounds are also included. Physiologically acceptable salts are also included. Preferably, the prostaglandin is PGE-1, PGE-2, PGF-2α, PGD-2, PGF-1α, and 15-methyl-PGF-2α. Most preferably, the prostaglandin is PGE-2 or PGE-1.

Preferably, the prostaglandin is administered topically, directly to the clitoris. Administration topically to the clitoris may be accomplished by applying an amount of a liquid, gel, or solid which contains an effective amount of the prostaglandin directly onto the clitoris. In the case when the prostaglandin is contained in a pharmaceutical composition which is a liquid, the administration may be accomplished by means of a dropper or syringe. The liquid solution may also be sprayed or delivered in an aerosol onto the clitoris. When the composition containing the prostaglandin is in the form of a gel, lotion, or cream the administration may be carried out by means of a tube, brush, swab or the finger tip. Pharmaceutical compositions which contain the prostaglandin and which are in the form of a solid may be administered by placing the appropriate amount of the solid directly on the clitoris or by dusting or spraying a powder.

Although the exact amount of prostaglandin to be administered will depend on the exact size and condition of the patient, the prostaglandin is suitably administered in an amount of 0.1 nanograms to 2,000 μg, preferably 1.0 nanogram to 500 μg. Specifically, when the prostaglandin is PGE-1, the PGE-1 is suitably administered in an amount of 20 nanograms to 2,000 μg, preferably 200 nanograms to 500 μg, per unit dosage. When the prostaglandin is PGE-2, the PGE-2 is suitably administered in an amount of 0.1 nanograms to 2,000 μg, preferably 1 nanogram to 500 μg, per unit dosage. These broad ranges of suitable dosages reflect clinical findings that various coagents and carriers can either increase or decrease the drug activity exhibited by a given mixture.

Typically, the prostaglandin will be administered 1 to 60 minutes, preferably 5 to 30 minutes, prior to the time when it is desired to commence sexual intercourse.

PGE-1, prostaglandin $E_1$, is also known as alprostadil or $PGE_1$. The formal chemical name of PGE-1 is 3-hydroxy-2-(3-hydroxy-1-octenyl)-5-oxocyclopentaneheptanoic acid, and the structure of PGE-1 is

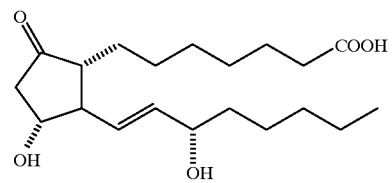

Prostaglandin $E_1$ may be isolated from sheep seminal vesicle tissue as described in Bergstrom et al., *Acta. Chem. Scand.*, vol. 16, p. 501 (1962) and *J. Biol. Chem.*, vol. 238, p. 3555 (1963). The synthesis of prostaglandin $E_1$ may be carried out as described in Corey et al., *J. Am. Chem. Soc.*, vol. 91, p. 535 (1969); Corey et al., *J. Am. Chem. Soc.*, vol. 92, p. 2586 (1970); Sih et al, *J. Am. Chem. Soc.*, vol. 94, p. 3643 (1972); Sih et al., *J. Am. Chem. Soc.*, vol. 95, p. 1676 (1973); Schaaf et al., *J. Org. Chem.*, vol. 37, p. 2921 (1974); and Slates et al., *Tetrahedron*, vol. 30, p. 819 (1974).

PGE-2, prostaglandin $E_2$, is also known as dinoprostone or $PGE_2$. The formal chemical name of PGE-2 is 7-[3-hydroxy-2-(3-hydroxy-1-octenyl)-5-oxocyclopentyl]-5-heptenoic acid, and the structure of PGE-2 is:

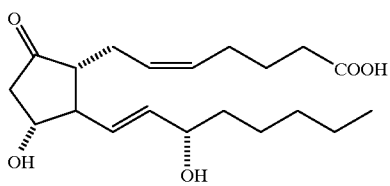

Prostaglandin $E_2$ may be isolated from sheep seminal vesicle tissue as described in Bergstrom et al., *Acta. Chem. Scand.*, vol. 16, p. 501 (1962). Prostaglandin $E_2$ may be synthesized as described in Corey et al., *J. Am. Chem. Soc.*, vol 92, p. 397 (1970); Corey et al., *J. Am. Chem. Soc.*, vol. 92, p. 2586 (1970); and Heather et al., *Tetrahedron Letters*, p. 2313 (1973).

Both prostaglandin $E_1$ and $E_2$ are commercially available from Sigma Chemical Company of St. Louis, Mo.

PGE-2 is also commercially available as a Prostin E-2 suppository and as Prepidil Gel from Pharmacia & UpJohn Company, Kalamazoo, Mich., and as Cervidil from Forrest Pharmaceuticals, Inc., St. Louis, Mo. These preparations are indicated for cervical ripening and contain between 0.5 and 20 mgs of PGE-2. No reports in the medical literature, *Physicians Desk Reference*, 51$^{st}$ Edition, Medical Economics, Montvale, N.J., 1997; or Goodman and Gillman's *The Pharmacologic Basis of Therapeutics*, 9$^{th}$ Edition, McGraw-Hill, 1996 can be found with respect to prostaglandins stimulating the female sexual response. Indeed, in labor induction as much as 1000–10,000,000 times the dose effective in the present method of PGE-2 is administered to the cervix without sexual stimulation ever being reported as a side effect.

PGF-2α, prostaglandin $F_{2\alpha}$, is also known as dinoprost or $PGF_{2\alpha}$. The formal chemical name is 7-[3,5-dihydroxy-2-(3-hydroxy-1-octenyl)cyclopentyl]-5-heptenoic acid. PGF-2α may be prepared as described in U.S. Pat. No. 3,657,327, which is incorporated herein by reference.

15-Deoxy-16-hydroxy-16-methyl-PGE-1 methyl ester is also known as misoprostol and has the formal chemical name of (±)-methyl-(1R,2R,3R)-3-hydroxy-2-[(E)-(4RS)-4-hydroxy-4-methyl-1-octenyl]-5-oxocyclopentaneheptanoate. 15-Deoxy-16-hydroxy-16-methyl-PGE-1 methyl ester may be prepared as described in U.S. Pat. No. 3,965,143, which is incorporated herein by reference.

Enprostil has the formal chemical name of [1α,2β(1E,3R*),3α]-7-[3-hydroxy-2-(3-hydroxy-4-phenoxy-1-butenyl)-5-oxocyclopentyl]-4,5-heptadienoic acid methyl ester. Enprostil may be prepared as described in U.S. Pat. No. 4,178,457, which is incorporated herein by reference.

PGI-2 is also known as prostacyclin, epoprostenol, prostaglandin $I_2$, prostaglandin X, $PGI_2$, and PGX. Prostacyclin may be prepared as described in U.S. Pat. No. 4,539,333, which is incorporated herein by reference.

The remaining prostaglandins are described in Alex Gringanz, *Introduction to Medicinal Chemistry*, Wiley-VCH, Inc., New York, pp. 158–159 and 641–642, 1997, which is incorporated herein by reference.

Cyclodextrin complexes of the prostaglandin may be used in order to increase the stability and efficacy. Cyclodextrin complexes may be prepared by adding the proper stoichiometric ratio of the prostaglandin to α, β, or γ cyclodextrin in an aqueous solvent and then either using as is or lyophilizing to provide a solid clathrate for mixing. These complexes are described in Yamamura et al, *J. Chromatogr.*, vol. 331, pp. 383–388 (1985); Hirayama et al, *Chem. Pharm. Bull.*, vol. 32 pp. 4237–4240 (1984); Uekama et al, *J. Pharm. Sci.*, vol. 73, pp. 382–384 (1984); and Yamamura et al, *J. Chromatogr.*, vol.303, pp. 165–172 (1984), which are incorporated herein by reference.

The prostaglandin may be administered alone or it may be advantageous to simultaneously administer or to pretreat the patient with one or more co-agents to increase the efficacy of the method. Examples of co-agents which may be coadministered include:

1. Agents which inhibit 15-hydroxyprostaglandindehydrogenase (PGDH);
2. ACE inhibitors, including but not limited to captopril, enalapril, enalaprilat, quinapril, lisinopril, and ramipril, may enhance the efficacy of the present method and decrease long term complications, such as inflammatory and fibrotic responses;
3. Nitro vasodilators, including but not limited to nitroglycerin, isosorbide dinitrate, amyl nitrate, isosorbide mononitrate, erythrityl tetranitrate, and sodium nitoprusside, may enhance the efficacy of the present method;
4. Alpha blockers, including but not limited to prazosin, phentolamine, phenoxybenzamine, dibenzamine, doxazosin, terazosin, trimazosin, tolazoline, corynthanine, rauwolscine, and piperoxan, are especially desirable for increasing the efficacy and prolonging the action of the present method;
5. Other adrenoreceptor agents, including but not limited to yohimbine, labetalol, carvedilol, and bucindolol, may also enhance the activity and prolong the action of the present method;
6. Phosphodiesterase (PDE) inhibitors, including but not limited to caffeine, aminophylline, theophylline, amrinone, milrinone, vesnarinone, vinpocetine, pemobendan, cilostamide, enoximone, peroximone, rolipram, R020–1724, zaniprast, dipyridamole, and sildenafil, may also be effective in enhancing the efficacy of the present method and for prolonging the effect;
7. Muscarinic agents such as pilocarpine, edrophonium, and bethanacol;
8. Dopaminergic agonists such as apomorphine and bromocriptine;
9. Ergot alkaloids such as ergotamine and ergotamine analogs, including acetergamine, bravergoline, bromerguride, clanegollone, ergonovine, ergotamine tartrate, and pergolide;
10. Opiate antagonists such as naloxone, naltrexone, nalmefene, nalorphine, methyl naltrexone, CTOP, diprenorphine, β-funaltrexamine, naloxonazine, norbinaltorphimine, natrindole, BNTX, and other analogs, which exhibit opioid antagonistic properties; and
11. Polypeptide neurotransmitters such as VIP, calcitonin, calcitonin gene related product, VIP analogs, and cholecystokinin and all its analogs such as CCK8.

Particularly desirable combinations are PGE and alpha-blockers, PGE and PGDH inhibitors, and PGE and PDE inhibitors. Any combinations of the single above-listed compounds or multiple combinations of different compounds or different groups may also be used. In some instances, it may be advantageous to pretreat with one or more of the co-agents. For example, pretreatment with a PGDH inhibitor followed by treatment with PGE will enhance the efficacy of the present method.

By the term "15-hydroxyprostaglandindehydrogenase inhibitor" it is meant any compound which exhibits a significant and selective inhibition of prostaglandin degrading enzyme, or 15-hydroxyprostaglandindehydrogenase (PGDH). Two forms of 15-hydroxyprostaglandindehydrogenase (PGDH) are known: Type I, which is $NAD^+$ dependent, and Type II, which is $NADP^+$ dependent. Type I operates at a Km one order of magnitude lower than Type II and is thus more significant physiologically. Type I PGDH is described in Mak et al, *Biochimica et Biophysica Acta*, vol. 1035, pp. 190–196 (1990); Ensor et al, *J. Lipid Mediators Cell Signalling*, vol. 12, pp. 313–319 (1995); and Berry et al, *Biochemical Pharmacology*. vol. 32, no. 19, pp. 2863–2871 (1983), which are incorporated herein by reference. Partially purified bovine lung Type I PGDH is commercially available from BDH, Limited (Poole, UK). Berry et al., Tai et al., Muramatsu et al., and Mak et al. describe assays for determining enzymatic activity of Type I PGDH as well as methods for determining the degree of inhibition of this enzyme.

Type II PGDH is described in Chang, et al, *Biochem. Biophys. Res. Commun.*, vol. 99, pp. 745–751 (1981); Jarabak, et al, *Prostaglandins*, vol. 18, pp. 241–246 (1979), and et al, *Biochem. Biophys. Res. Commun.*, vol. 81, pp. 1227–1234 (1978), all of which are incorporated herein by reference.

Examples of suitable 15-hydroxyprostaglandindehydrogenase inhibitors include but are not limited to glycyrrhizic acid, licorice, glycyrrhetinic acid, various glycosides of glycrrhetinic acid, carboxenolone, DHEA, spironolactone, sofalcone, indomethacin, sulindac, etodolac, oleic acid, palmitic acid, and sulphasalazine and analogues thereof. Antibodies which bind to and inhibit Type I PGDH may also be used.

Glycyrrhizic acid is also known as glycyrrhizin, glycyrrhizinic acid, and glycyrrhetinic acid glycoside. The formal chemical name is 20β-carboxy-11-oxo-30-norolean-12-en-3β-yl-2-O-β-D-glucopyranuronosyl-α-D-glucopyranosiduronic acid, and the structure is:

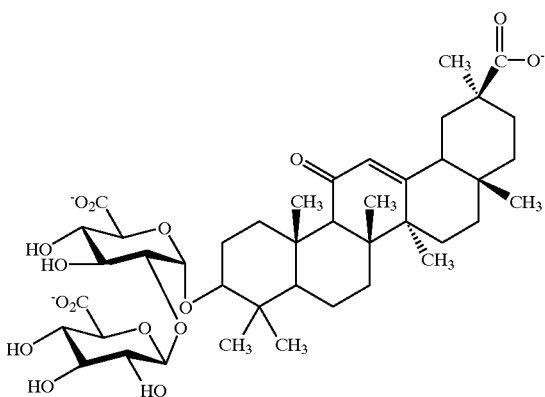

Glycyrrhizic acid is commercially available from Sigma Chemical Company of St. Louis, Mo.

Glycyrrhetinic acid is unglycosylated glycyrrhizic acid, and its structure is:

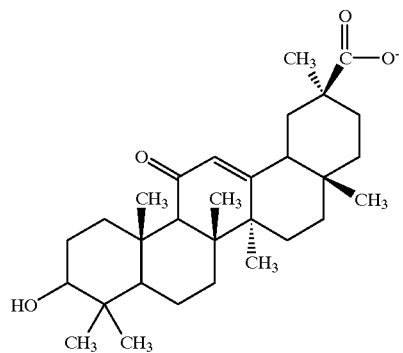

Glycyrrhetinic acid may be obtained from licorice extract.

Carbenoxolone is also known as 3β-hydroxy-11-oxo-20β-olean-12-en-29-oic acid hydrogen butanedioate and has the following structure:

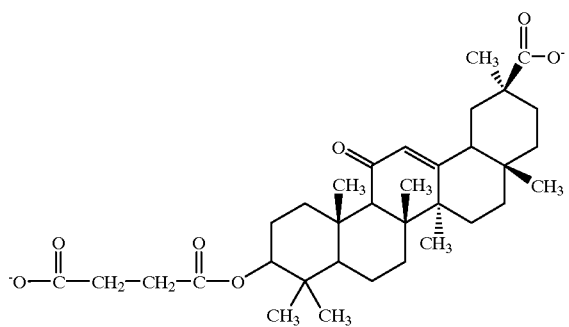

Carbenoxolone may be synthesized as described in U.S. Pat. No. 3,070,623, which is incorporated herein by reference.

Licorice is also known as sweet root liquorice and glycyrrhiza and is described in the Merck Index, 10th edition, citation 4368 as "glycyrrhiza, Licorice, liquorice; sweet root. Dried rhizome and root of *Glycyrrhiza glabra* L., var. typica Regel & Herder (Spanish licorice), or of *G. Glabra* L., var. *glandulifera* (Waldst. & Kit.) Regel & Herder (Russian licorice), or of other varieties of G. g yielding a yellow and sweet wood, Leguminosaw. Habt. Southern Europe to Central Asia. Constit. 6–14% glycyrrhizin (the glucoside of glycyrrhetic acid), asparagine, sugars, resin."

Licorice is a crude preparation prepared from dried rhizomes or roots and as such contains large numbers of compounds many of which are not identified. A simple aqueous extract of a commercially available dried licorice root preparation may be prepared as follows. Two grams of this dried licorice root was mixed with 10 mls of distilled water, stirred until thoroughly mixed at room temperature and filtered to remove particulate matter. This simple aqueous extract of licorice is effective in inhibiting PGDH and may be used as is in the present invention.

Spironolactone is also known as Aldactone A or Verospiron. The formal chemical name of spironolactone is 17-hydroxy-7-mercapto-3-oxo-17α-pregn-4-ene-21-carboxylic and γ-lactone, 7-acetate, and the structure is:

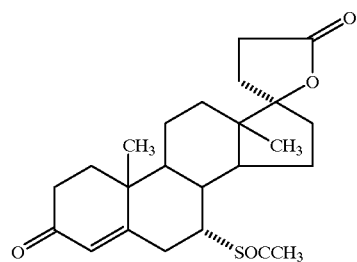

Spironolactone is commercially available from Sigma Chemical Company of St. Louis, Mo.

Sofalcone is formally known as [5-[(3-methyl-2-butenyl)oxy]-2-[3-[4[(3-methyl-2-butenyl)oxy]phenyl]-1-oxo-2-propenyl]phenoxy]acetic acid and has the formula:

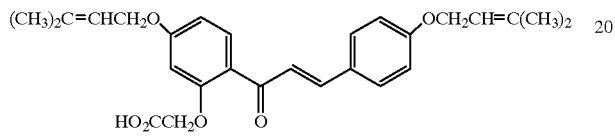

Sofalcone may be prepared as described in U.S. Pat. No. 4,085,135, which is incorporated herein by reference.

DHEA is formally known as 3-hydroxyandrost-5-en-17-one or dehydroepiandrosterone or prasterone. The structure of DHEA is:

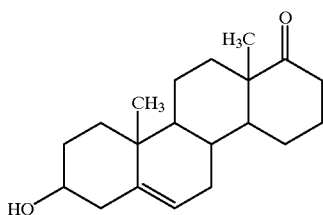

DHEA may be prepared as described in H. Hosoda et al, *J. Org. Chem.*, vol. 38, p. 4209 (1973), which is incorporated herein by reference.

Sulfasalazine is also known as 2-hydroxy-5[[4-[(2-pyridinylamino)sulfonyl]phneyl]azo]benzoic acid and has the structure:

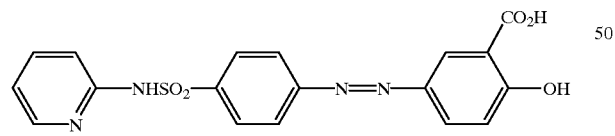

A number of sulfasalazine analogs have been shown to be inhibitors of PGDH by Berry et al, *Biochemical Pharmacology*, vol. 32, pp. 2863–2871 (1983). Examples of sulfasalazine analogs which may be used as the PGDH inhibitor in the present compositions include:

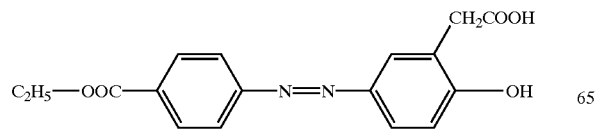

-continued

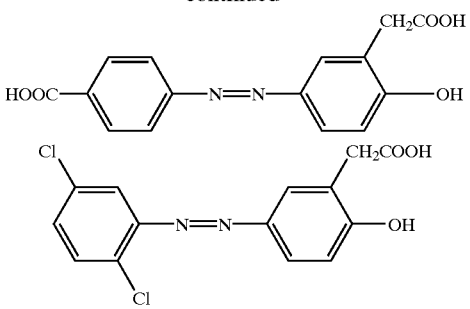

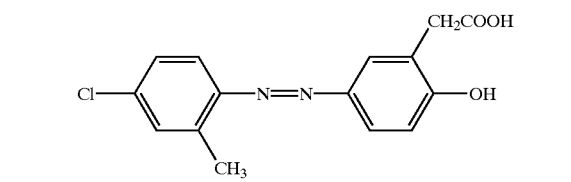

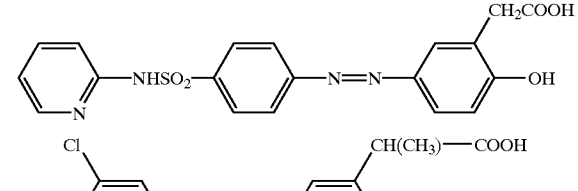

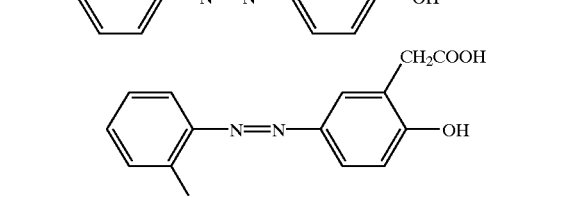

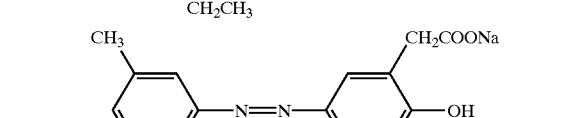

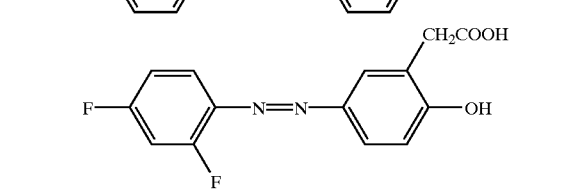

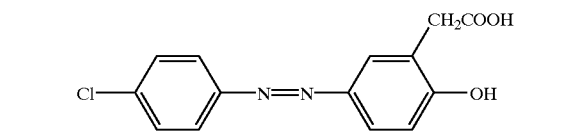

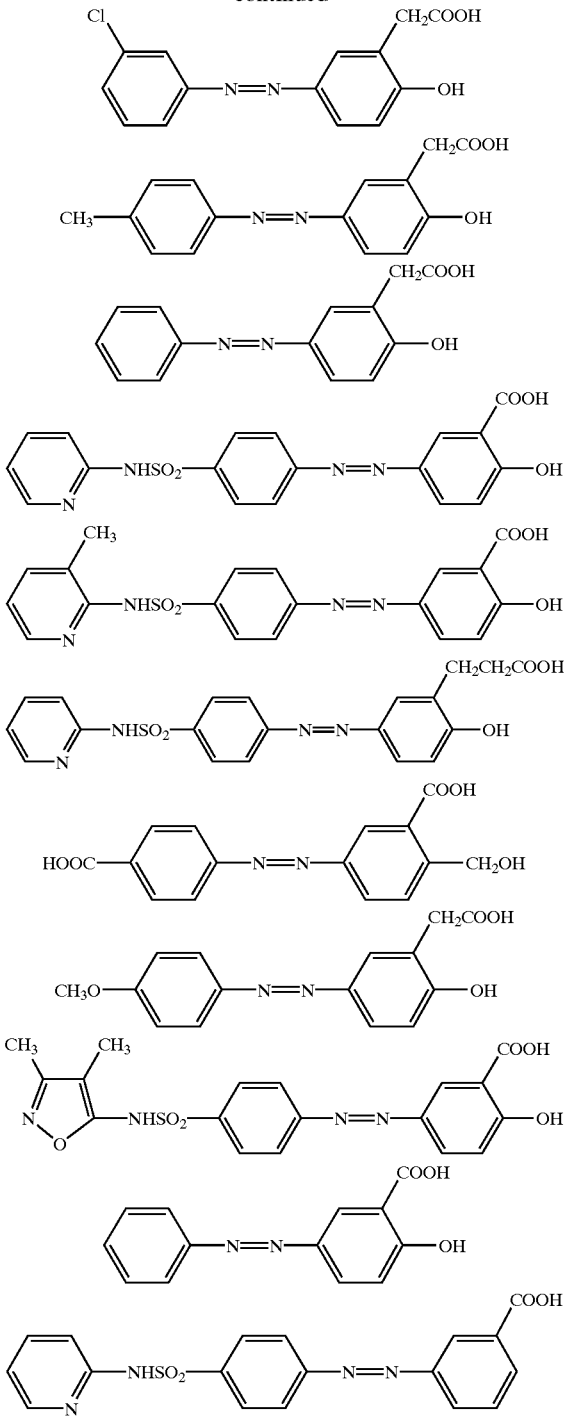

Etodolac is also known as 1,8-diethyl-1,3,4,9-tetrahydropyrano-[3,4-b]indole-1-acetic acid. Etodolac may be prepared as described U.S. Pat. No. 3,843,681, which is incorporated herein by reference.

Indomethacin is also known as 1-(4-chlorobenzoyl)-5-methoxy-2-methyl-1H-indole-3-acetic acid. Indomethacin may be prepared as described in U.S. Pat. No. 3,161,654, which is incorporated herein by reference.

Sulindac is also known as 5-fluoro-2-methyl-1-[[4-methylsulfinyl)phenyl]methylene]-1H-indene-3-acetic acid.

Sulindac may be prepared as described in U.S. Pat. Nos. 3,654,349 and 3,647,858, which are incorporated herein by reference.

The 15-hydroxyprostaglandindehydrogenase inhibitor will typically be present in an amount of 25 to 100, preferably 50 to 100, pig clitoral units of PGDH inhibition activity, per unit dosage. The amount of inhibitor which corresponds to a unit of pig clitoral PGDH inhibition activity is determined using either the spectrophotometric or radio-chemical assay described in the Examples. For inhibitors which exhibit a significant absorption at 340 nm, it is preferred to use the radio-chemical assay.

In a second embodiment, the present invention provides novel pharmaceutical compositions which are useful for enhancing female sexual desire and responsiveness. The present pharmaceutical compositions are characterized as containing: (a) a prostaglandin; (b) a pharmaceutically acceptable carrier; and having a pH of 3 to 7, preferably 4 to 6. In cases in which an aqueous component is present, one may simply add a sufficient amount of a pharmaceutically acceptable acid or base, e.g., HCl or NaOH to adjust the pH to the desired value. For nonaqueous compositions, one may add to each unit dose the residual powder from 0.5 ml of a 0.01 Molar aqueous solution of a pharmaceutically acceptable citrate salt, e.g., sodium citrate, which has the desired pH. For example, 0.5 ml of 0.01 Molar sodium citrate at pH 4.5 is lyophilized, and the powdered residue is added to a unit dose of PGE-2 in polyethylene glycol (PEG) MW 1450. Upon contact of this dose with a mucosal membrane, the lyophilized citrate will dissolve and buffer the pH of the mucosal fluid to about pH 4.5 and thereby enhance the activity of the PGE-2 as the PEG pellet dissolves.

In a preferred embodiment, the present composition further comprises: (c) an antioxidant selected from the group consisting of citrate salts and tocopherol. It has been found that prostaglandins, in particular PGE-2, are especially stabile when formulated in a composition which contains a citrate salt, such as sodium, potassium, or ammonium citrate, or tocopherol. Typically, the present pharmaceutical composition will contain 1 to 2,000 μg, preferably 50 to 1,000 μg, of the citrate salt, or 20 to 2,000 μg, preferably 50 to 1,000 μg, of tocopherol. Particularly good results have been achieved when the prostaglandin is present in a 1 millimolar sodium citrate aqueous solution or in liposomal solution which also contains 1 mg per ml of tocopherol as an antioxidant.

The present compositions may also contain the same coagents described above in the context of the present method. Thus, the present compositions may contain one or more agents which block prostaglandin degrading enzymes, one or more ACE inhibitors, one or more muscarinic agents, one or more adrenoreceptor agents, one or more dopamine agonists, one or more opiate antagonists, one or more nitrates or nitroso compounds, one or more polypeptide neurotransmitters, and/or one or more agents which inhibit phosphodiesterase.

The present pharmaceutical composition can be in any conventional form, such as a liquid, solid or gel. Examples of suitable liquids include sterile solutions, suspensions, and emulsions, including creams, ointments, and liposomes. For oil based or lipophilic preparations, other suitable anti-oxidants include BHT. For water based or hydrophilic preparations, other suitable anti-oxidants include ascorbic acid and its sodium and potassium salts. Preferred PEG suppositories contain a PEG which is solid at ambient or room temperature but rapidly dissolves/melts when placed on the clitoris. Good results have been achieved using isotonic aqueous solutions which contain sodium citrate.

Examples of suitable solids include polyethylene glycol (PEG), polyethylene oxide and other low melting point or water-soluble polymers including fatty acid esters made into suppositories or pellets. Examples of suitable gels include triacetin, hydroxycellulose, gels composed of water, propylene glycol, hydroxypropyl methylcellulose and any other gels which are compatible with the prostaglandin. Liposomal mixtures are particularly preferred as they tend to induce a stronger effect at a given dose of prostaglandin and stabilize the prostaglandin. A commercially available liposome to which the prostaglandin can be added is Liposyn II™ 10% or 20% sold by Abbott Laboratories, North Chicago Ill. The liposomes may be prepared as either anionic or cationic liposomes depending upon the prostaglandin and any co-agent present in order to maximize the desired effect. A particularly preferred gel is lecithin organogel prepared according to H. Willimann et al, "Lecithin organolgel as matrix for transdermal transport of drugs," *J. Pharm. Sci.*, vol. 81(9), pp. 871–874 (1992). This particular preparation exhibits a dramatically enhanced potency.

One may also use a gel in which one or more of the prostaglandins or co-agents is released in a controlled-released manner (i.e., released over time) to prolong the effect of the composition. For example, PGE can be formulated into a cross-linked polyethylene oxide/urethane polymer which is well tolerated by living tissues and releases the prostaglandin in a controlled release manner. Controlled release compositions are disclosed in D. H. Lewis, *Controlled Release of Pesticides and Pharmaceuticals*, Plenum Press, New York, 1981; and A. F. Kydonieus, *Controlled Release Technologies: Methods, Theory, and Applications*, CRC Press, Boca Raton, 1980, which are incorporated herein by reference.

In another preferred embodiment, the present composition is in the form of a solution in which the prostaglandin with or without a PGDH inhibitor or coagent is dissolved or suspended in 1,2,3-propanetriol triacetate, triacetin. Triacetin is a well known solvent and is commercially available from Aldrich Chemical Company, St. Louis, Mo. This composition enhances the drug potency dramatically and chemically stabilizes the prostaglandin at room temperature. Other similar short-chain triglycerides with alkyl chains from $C_{1-6}$ are expected to have similar beneficial effects. These compounds are available from Sigma Chemical Company (St. Louis, Mo.).

Typically, the present pharmaceutical composition will contain the prostaglandin in a concentration such that an effective amount of the prostaglandin is delivered to the clitoris with a single application of the composition. For example, in the case of a liquid, the composition will contain sufficient prostaglandin such that an effective amount of the prostaglandin is delivered to the clitoris by application of a drop (0.01 to 0.30 ml) of the liquid. Thus, the present compositions, when in the form of a liquid will suitably contain 10 nanograms/ml to 1,500 µg/ml, preferably 100 nanograms/ml to 1,000 µg/ml, of the prostaglandin. In the case of a suppository, the suppository will preferably contain sufficient prostaglandin such that an effective amount of the prostaglandin is delivered to the clitoris by application of a single suppository to the clitoris. Suppositories according to the present invention typically have volumes of 0.01 to 0.30 ml, preferably 0.1 to 0.2 ml. Thus, pharmaceutical compositions according to the present invention which are in the form of a suppository will suitably contain the prostaglandin in a concentration of 10 nanograms/ml to 1,500 µg/ml, preferably 100 nanograms to 1,000 µg/ml. Similarly, when the composition is in the form of a gel, the gel will typically contain sufficient prostaglandin such that an effective amount of prostaglandin is delivered to the clitoris upon application of a single dose (0.01 to 0.60 ml, preferably 0.05 to 0.40 ml) of the gel to the clitoris. Thus, the gels of the present invention will suitably contain the prostaglandin in a concentration of 10 nanograms/ml to 1,500 µg/ml, preferably 100 nanograms to 1,000 µg/ml. Since drug dosages typically vary from person to person, repeated applications may be used to achieve the desired effect.

When the prostaglandin is prostaglandin $E_1$, the pharmaceutical composition will suitably contain the prostaglandin $E_1$ in an amount of 20 nanograms to 2,000 µg, preferably 200 nanograms to 500 µg, per unit dosage. When the prostaglandin is prostaglandin $E_2$, the pharmaceutical composition will suitably contain the prostaglandin $E_2$ in an amount of 0.1 nanograms to 2,000 µg, preferably 1.0 nanograms to 500 µg, per unit dosage.

In a third embodiment, the present invention provides kits which are useful for enhancing female sexual desire and response. The present kits are characterized as containing: (a) a means for containing a prostaglandin or pharmaceutical composition containing the prostaglandin; and (b) means for administering the prostaglandin or pharmaceutical composition containing the prostaglandin to the clitoris. The means for containing the prostaglandin or pharmaceutical composition containing the prostaglandin may be a vial, a bottle, a pouch, an envelope, a can, a tube, an atomizer, an aerosol can, etc. The means for administering the prostaglandin or pharmaceutical composition containing the prostaglandin to the clitoris may be a dropper, a swab, a stick, or the nozzle or outlet of an atomizer or aerosol can. It is to be understood that the means for administering the prostaglandin or pharmaceutical composition containing the prostaglandin to the clitoris may be connected to or a part of the means for containing the prostaglandin or pharmaceutical composition containing the prostaglandin. For example, the containing means may be an atomizer or an aerosol can, and the administering means may be the nozzle or outlet of the atomizer or the aerosol can.

Examples of preferred kits include:

A. A kit which includes a container which can hold 1 to 100 unit doses of the prostaglandin or the pharmaceutical composition containing the prostaglandin and a dropper which can dispense between 0.01 to 0.6 ml as a unit dose. The container is preferably glass, metal, or a plastic known not to adsorb hydrophobic compounds.

B. A kit which includes a container which can hold 1 to 100 unit doses of the prostaglandin or the pharmaceutical composition containing the prostaglandin with a spray or aerosol applicator to spray the prostaglandin or pharmaceutical composition onto the clitoris. The container is preferably glass, metal, or a plastic known not to adsorb hydrophobic compounds.

C. A kit which includes a tube which holds 1 to 100 unit doses of a pharmaceutical composition containing the prostaglandin, which is in the form of a cream or gel, and an applicator which can dispense a unit dose of the composition.

D. A kit which includes 1 to 100 unit doses of pellets, film or suppositories containing a pharmaceutical composition comprising the prostaglandin and each individually wrapped in foil and sealed to protect the prostaglandin from the air. The foil is preferably opaque to eliminate the degrading effects of light on the prostaglandin.

E. A kit which includes 1 to 100 unit doses of a pharmaceutical composition which comprises the prostaglandin and which have been lypholized and sealed under inert gas in an ampoule or vial. Lyophilized compositions typically exhibit a much longer shelf life than other forms and may be reconstituted close to the time of use so that degradation of the prostaglandin is minimized. The kit may also include a suitable diluent, syringe and needle, and/or alcohol swabs.

The present kits will also typically include means for packaging the container means and the administering means. Such packaging means may take the form of a cardboard or paper box, a plastic or foil pouch, etc. The present kits will also usually include written instructions which describe how to administer the prostaglandin or pharmaceutical composition containing the prostaglandin to the clitoris. It is to be understood that the written instructions may be on any of the container means, the administering means, or the packaging means, in addition to being present on a separate piece of paper.

In another embodiment, the present invention provides novel methods of diagnosing sexual dysfunction in a female. The present method of diagnosing female sexual dysfunction involves monitoring the baseline clitoral temperature of the clitoris in a female, administering a prostaglandin agent, known to cause a sexual response when applied to a clitoris, to the clitoris of said female, measuring the clitoral temperature response of said female to said administering, and comparing said clitoral temperature response of said female to that found in females not suffering sexual dysfunction.

Other features of the present invention will become apparent in the course of the following descriptions of exemplary embodiments which are given for illustration of the invention and are not intended to be limiting thereof.

EXAMPLES

I. Formulations
General Instructions

The composition should be sterilely prepared and stored. Prostaglandins are degraded by high temperatures. Therefore, the compositions should be stored between 38–45° F. Freezing a liquid composition may degrade the prostaglandin, so storage of frozen compositions for long periods of time should be avoided. The composition should also be protected from light. The prostaglandin may have an adverse effect on children and pregnant women. So the present compositions should be kept away from children and not used by pregnant women.

The clitoris is often retracted or hidden under the clitoral hood. Thus, prior to administration of the present composition, the clitoral hood should be retracted with the finger of one hand, and the clitoral hood should be held back as the dose is applied.

A. Water-Soluble Prostaglandins, Prostaglandin Salts, and Prostaglandin Complexes 5 mg of PGE-2 is added to sterile cold water (10 ml, 1 mM in sodium citrate), stirred until dissolved and the pH adjusted with either NaOH or HCl, to a pH of about 5.4. The resulting composition was dispensed using any of the kits. For kit E, the aqueous PGE-2 solution is rapidly frozen in the vial using dry ice or liquid nitrogen and lypholized using a hard vacuum (<0.001 Torr), then covered with anhydrous nitrogen (other inert gases may be used), and sealed with a septum. This procedure can be used for any prostaglandin which is water soluble. Using the same procedure, fresh aqueous solutions of prostaglandin can be prepared with isotonic saline or any water-soluble compound desired. For example, lactose may be used instead of saline. PGE-1 is soluble to the extent of 80 µg/ml in water and has been used in this method of composition preparation. PGE-1 α-cyclodextrin complex and PGE-2 β-cyclodextrin complex are more water-soluble and chemically stable than either free prostaglandin, and may also be used in this method.

B. Aqueous Solutions with a Coagent

To prepare aqueous solutions of a prostaglandin and a coagent, one may combine aqueous solutions of the components in the proportion necessary to give the final desired concentration or add the desired aqueous diluent to the pure components and mix. For example, 1 mg of PGE-2 was dissolved in 10 ml of an aqueous solution of 1 mM sodium citrate, and then 300 mg of papaverine HCl was added. The resulting mixture was stirred until all the components dissolved. Then 15 mg phentolamine HCl were added, and the mixture was stirred until all components were dissolved, and the pH of the resulting solution was adjusted to about 5.4. This solution, containing 100 µg of PGE-2, 30 mg of papaverine, and 1.5 mg of phentolamine HCl per ml, may then be used in any of the compatible kits above as is or lypholized and used in Kit E. Alternatively, 1 ml of aqueous PGE-2 (1.0 mg/ml), 5 ml of aqueous 60 mg/ml papaverine HCl, 1 ml of aqueous phentolamine HCl (1.5 mg/ml), and 3 ml water may be combined and mixed to produce the same solution. As stated above in Procedure A, one may use aqueous solutions of any compatible compound. For example, isotonic saline, 1 mM sodium citrate, or isotonic lactose may also be used.

C. Liposomal Solutions

Either an aqueous or oil-based solution of the prostaglandin and a coagent can be added to a liposomal mixture of, for example; 10 gm of safflower oil, 10 gm of soybean oil, 1.2 gm of egg phosphotides, and 2.5 gm of glycerin in a final volume of 100 ml (the remainder being water). Addition of 1 mg/ml of tocophenol stabilizes the prostaglandin. 2 mg of PGE-2, 10 mg of tocopherol, and 2 mg of Naloxone HCl may be added to 10 ml of this prepared liposomal solution, and the resulting mixture is stirred until all the components are dissolved. The pH of the resulting solution is then adjusted to about 5.4. This solution may then be used in any of the kits listed above or lyophilized and used in Kit E. Alternatively, liposomal mixtures of PGE-2 and coagents may be prepared as outlined in R. C. MacDonald et al, *Biochem. Biophys. Acta.*, vol. 1061, p. 297 (1991), which is incorporated herein by reference.

Liposomal solutions are particularly favored for compounds with limited solubility in water. They also increase stability of the prostaglandin, decrease burning sensation, and lower the dose of the prostaglandin needed.

D. Organogel Preparation

Organogels are excellent as a matrix for transdermal transport of drugs (H. Willimann et al, *J. of Pharmaceutical Sciences*, vol. (9), pp. 871–874 (1992). 3.0 mg of PGE-2 and 3.0 mg of prazosin HCl were dissolved in 1.0 ml of isopropyl myristate and 100 mg of soybean lecithin (high purity from Signa Chemical, St. Louis). Then, 40 µl of water were slowly added with agitation to produce a thick viscous gel. This may be used in any appropriate kit listed above. Utilization of a prostaglandin cyclodextrin complex in an organogel is particularly preferred.

E. Pellets and Suppositories

Any suitable matrix material may be used such as polyethylene glycol (PEG), PEG-ethers, polyethoxylene glycols, and long chain fatty acid esters so that a dose is produced which either melts at body temperature or dissolves in water. For example, 2.0 mg of PGE-2 is melted in 20 mg of PEG-1450 and formed, while molten, into cylindrical pellets or drops and allowed to cool. Each 1 mg pellet contains 100 µg of PGE-2. By changing the weight of the pellet, one may easily produce a unit dose of prostaglandin of any size. Coagents which are not soluble in PEG or molten at 50–55° C. may be suspended in the molten PEG-prostaglandin mixture to give a solid suspension, which is formed into as pellets or drops as described above. Buffered lyophilized sodium citrate powder may be added to give an enhanced effect on contact with a mucosal membrane. Ethyl stearate forms a good solid matrix at room temperature which will melt at body temperature.

F. Non-Aqueous Liquids and Gels

It has been found that short-chain triglycerides impart a dramatic and unexpected increase in the potency of the prostaglandin. The effects of triacetin as a carrier are described in Section V where an increase in PGE potency of several orders of magnitude are observed. Such triglycerides are expected to increase the chemical stability of prostaglandins during storage, thus imparting a room-temperature shelf life to these delicate compounds. Any of the trigylcerides may be effective in this manner. Short-chain ($C_{1-6}$ alkyl chains) triglycerides are particularly desired for preparations that are liquid at room temperature. Higher melting triglycerides can be selected to produce a gel-like composition.

II. PGDH Activity

A. Pig Clitoral Preparation: Fresh sow external genitalia from sexually mature animals are obtained from a local slaughter house. The excised external genitalia are immediately washed in tap water and then in normal saline. The clitoris is then exposed by retracting the clitoral hood if necessary and the glans clitoridis which corresponds to the free extremity of the clitoris is separated from the rest of the genitalia by sharp dissection. The length in millimeters and the weight in milligrams of the glans clitoridis are measured and recorded. The entire glans clitoridis is homogenized with four volumes of an ice-cold 100 mM potassium phosphate buffer (pH 7.5) containing 1 mM EDTA. Following centrifugation at 15,000 g for 15 minutes, the resultant supernatant fraction is used as the enzyme source of the clitoral mucosa.

B. 15-Hydroxyprostaglandindehydrogenase (PGDH) Activity Determination:

Spectrophotometric Analysis

As a substrate, prostaglandin $E_1$ is incubated with the pig clitoral enzyme prepared above. The reaction mixture is contained in a total volume of 2.0 ml of the same buffer used above for the preparation of the pig clitoral preparation.

Prostaglandin $E_1$ (50 microM) and NAD (300 microM) are used as substrates. The reaction is initiated by the addition of the prostaglandin $E_1$. Incubation is done at 37° C. and is terminated by the addition of 0.5 mL of 2 NaOH. The oxidation of the prostaglandin is assayed by monitoring the reduction of NAD+ at 340 nanometers in a spectrophotometer. Reaction times are adjusted so that the initial quantity of prostaglandin is oxidized by 50 to 80%.

Radiochemical determination: The same reactions conditions listed for spectrophotometric analysis are used except that (5, 6, 8, 11, 12, 14, 15(n)-$^3$H)-prostaglandin $E_2$ (specific activity, 171 Ci, mmol) from Dupont de Nemours is used as a typical substrate. Any other tritiated prostaglandin substrate can be utilized in this assay. To terminate the reaction, methanol precipitation (75% volume/volume)) is performed; then, water is added to dilute the methanol to 10 volume percent. Soluble phase extractions are performed using octadecyl 18-C silica cartridges (J. T. Baker, Deventer, Holland). Dried extracts are run on 20×20, 60 A silica plates using the organic phase of ethyl acetate/acetic acid/isooctane/water (11:2:5:10). Authentic prostaglandin $E_2$, 15-keto-prostaglandin $E_2$, and 13, 14-dihydro-15-keto-prostaglandin $E_2$ are comigrated on separate lanes. After localization of the compounds using phosphomolybdic spray, the silica is scraped, and the respective amounts of prostaglandin $E_2$ and 15-keto-prostaglandin $E_2$ are determined by radioactive counting. A mU is defined as that amount of enzyme which oxidizes 1 n mole of prostaglandin $E_2$ per min at 37° C., pH 7.5. The number of mU PGDH per mm of pig clitoris is then calculated by dividing the total number of mU by the mm of clitoris used to prepare the enzyme.

III. PGDH Inhibitor Activity Determination

In the context of the present invention, one pig clitoris unit of PGDH inhibition activity is defined as the quantity of inhibitor that prevents one percent of the quantity of prostaglandin present from being oxidized, using the assay described below on a pig clitoris of 5 mm.

Spectrophotometric: Using the above listed spectrophotometric analytical system for PGDH activity, the inhibitor in question is added to the reaction mixture prior to the addition of the prostaglandin $E_1$. At termination of the reaction, the quantity of the prostaglandin $E_1$ degraded is calculated and compared to the reaction without the inhibitor. Percent inhibition is defined as B/A×100 where A=nmoles of prostaglandin oxidized without inhibitor.
B=nmoles prostaglandin oxidized with inhibitor.

For example, if A=50 nmoles and B=25 nmoles with inhibitor C, then inhibitor C gives 25/50×100 or 50% inhibition in this assay.

Radiochemical Determination: The assay for inhibition is run with and without inhibitor added as listed above in the determination of PGDH activity radiochemically. A given inhibitor is added to the reaction mixture just prior to the addition of the prostaglandin $E_1$ being analyzed and the analysis performed as listed. The quantity of prostaglandin oxidized is calculated and interpreted as listed above for spectrophotometric analysis of inhibitor activity.

IV. Subjective Examples

Example 1

A. Two drops of an aqueous solution containing 20 $\mu$g of prostaglandin $E_2$, 150 $\mu$g of phentolamine hydrochloride, and 3 mg of papaverine hydrochloride in a liposomal solution was applied directly to the clitoris of a 41 year old female with no history of sexual dysfunction, using a dropper. Within one minute the subject reported a pleasurable tingling in her genitals. In the next two to three minutes, increasing sexual feelings were noted in the clitoris and generally throughout the subject's body. In addition, the clitoris became engorged and vaginal lubrication was noted in the same time frame without any stimulation other than the administration of the present composition. The subject reported multiple orgasms upon coitus, which represented an unusual and increased response for her.

B. The same 41 year old female had 2 drops of an aqueous solution containing 125 $\mu$g of PGE-2 and 125 $\mu$g of phentolamine applied to her clitoris with essentially the same response as in part A.

C. The same female had 3 drops of an aqueous saline solution containing 125 $\mu$g of PGE-2 applied to her clitoris and had the same response described in part A but with reduced intensity.

This Example illustrates the efficacy of using a prostaglandin, the additive effect of coadministering a coagent, and the increased activity associated with liposomal mixtures.

Example 2

Two drops of an aqueous solution containing 50 μg of prostaglandin $E_2$ and 150 μg of phentolamine hydrochloride was applied directly to the clitoris of a 32 year old female with no history of sexual dysfunction, using a dropper. The subject reported warm tingling sexual feelings in her clitoris within one minute. Clitoral engorgement ensued in the next several minutes along with increasing feelings that the subject identified as most similar to those that she normally experiences with sexual stimulation. The stimulation peaked at around 15 minutes after application of the composition. The subject rated the intensity of her response at eight (8) on a scale of one (1) to ten (10), with ten being the highest. Both the observable clitoral enlargement and the feeling of sexual excitement were gone within one hour after application of the composition. Repeat dosing at one and a half hours after the first dose gave the same response as the first dose.

Example 3

A pellet containing 70 μg of prostaglandin $E_2$ and 70 μg of phentolamine hydrochloride distributed in 1.4 mg of MW 1450 polyethyleneglycol (PEG) was applied directly to the clitoris of a 41 year female with no history of sexual dysfunction. The result was similar to those observed in Example 1.

Example 4

A pellet containing 70 μg of prostaglandin $E_2$ distributed in 1.4 mg of MW 1450 PEG was applied directly to the clitoris of a 41 year old female with no history of sexual dysfunction. The results were similar to those observed in Example 1.

Example 5

Three drops of a liposomal solution containing 150 μg of PGE-2 were applied directly to the clitoris of a 37 year old female with a history of decreased sexual responsiveness. The patient reported warm sexual feelings in her genitalia and had increased genital lubrication and sexual receptiveness. On intercourse, she had an orgasm and reported that she felt that the drops had greatly increased her sexual desire and responsiveness.

Example 6

A 41 year old female with a history of decreased sexual responsiveness and anorgasmia secondary to paroxetine took 50 mg of naltrexone HCl 2 hours before sex and then placed two (2) drops of a liposomal mixture containing 300 μg of PEG-2 on her clitoris. She described tingling sexual feelings in her pelvis and the spreading of the feeling over her body within 1 minute. She noticed a remarkable generalized feeling of sexual receptivity and, upon subsequent coitus, had the best sexual experience of her life.

Conclusions from Subjective Examples

The above-listed examples are given to illustrate a few of the possible applications of the invention. A number of women have been treated and evaluated. Overall, the results indicate a response rate of approximately 70% utilizing various drug doses and combinations similar to these examples. It is impossible to predict with certainty whether any given patient will respond to a given treatment for female sexual dysfunction. Some patients did not respond to any treatment. In general, it appears that women with diabetes mellitus that is poorly controlled and women on some psychiatric drugs known to cause sexual dysfunction are less likely to respond to the present method.

The following Examples illustrate methods for evaluating female sexual dysfunction and determining the response to a given treatment.

V. Blood Flow, Thermographic, and Subjective Examples

A. Methods

1. Measurement of clitoral blood flow by ultrasound:

Clitoral blood flow was estimated by utilizing the Knoll-Midas ultrasonic Doppler velocitometer (Urometrics, Inc.). The ultrasound probe was manually positioned over the middle of the clitoral body as it courses superficially through the perineum between the external vaginal opening and the end of the clitoris (glans clitoris). Each measurement was taken when the arterial pulse profile as displayed in real-time on the video screen was optimized. This method is analogous to that used in measuring the cavernosal artery velocity in the penis. The clitoral artery was easily visualized. Measurements were made at baseline and at various time intervals following the application of a drug to the clitoris. Peak systolic blood flow at baseline was compared to peak systolic blood flow following drug administration as a method of comparing relative efficacy in inducing clitoral artery vasodilatation in a manner analogous to studies of such drugs in men. Ultrasonic blood flow data in a single patient (Patient #1 shown in table) demonstrates good correlation between increases in clitoral artery peak systolic blood flow and increases in clitoral skin temperature.

2. Measurement of clitoral skin temperature:

A highly sensitive thermocouple capable of determining changes in skin temperature of 0.002 degrees Fahrenheit was connected to a computer-based recording device (F1000 by Focused Technology, Inc.) and used to measure changes in clitoral skin temperature. The patient changed from her clothes into a gown and was placed in a semi-reclining position in a comfortable recliner. Room temperature was controlled at 76 degrees F. (±1) and no air drafts were present. The thermocouple was coated with a small amount of lubricating jelly and placed in a labial skin fold adjacent to the clitoris. A period of equilibration (~15 minutes) allowed the measured temperature to stabilize. Next, precise doses of various pharmaceuticals were applied as solutions directly to the clitoris by a calibrated micropipette (Justor 1100DG, Sigma; St. Louis, Mo.). Typical volumes used were 20–50 microliters. Clitoral temperatures were continually measured and printed for analysis. Increases in skin temperature directly correlate with changes in cutaneous blood flow. See Birnbaum (U.S. Pat. No. 4,311,707) for an example of using this method to compare the relative vasodilatory potency of topical prostaglandins. Changes in skin temperature are reported as maximum recorded temperature in an interval minus the temperature at the end of the equilibration period. The magnitudes of these recorded temperature changes may be used as a measurement of the change in clitoral blood flow.

3. Patient Subjective Reports:

Patient reports of symptoms and effects of agents on sexual arousal measures (such as warmth and tingling, vaginal lubrication and excitation) were recorded. Blood pressure and pulse were also recorded. Different drugs were given on different days. Some series of drug titrations were recorded on several days.

B. Drug Solutions

1. Solutions of prostaglandin E-1 and E-2 were prepared by dissolving weighed amounts of the prostaglandin in triacetin to produce a concentrated stock solution. Serial dilutions of this stock solution were made by a micropipette. Since triacetin can partially hydrolyze on standing to produce traces of acetic acid, the triacetin was treated with a small amount of a concentration potassium bicarbonate solution to remove any acetic acid, then dried with magnesium sulfate and filtered to give a triacetin free of acid or water. Solutions were used the same day that they were made. Concentrations of prostaglandin varied from 2.0–1,000 micrograms per milliliter of triacetin. Following equilibration of clitoral temperature, a dose of triacetin was applied to the clitoris prior to active drug solutions to determine the effect of the carrier on the clitoris.

2. R-alphamethylhistamine hydrochloride is not soluble in triacetin but is soluble in saline. Normal saline +2 millimolar potassium phosphate at pH 7.4 was used to prepare solutions of R-alphamethylhistamine hydrochloride with concentrations from 2.5–100 micrograms per milliliter of saline.

C. Patients

1. Patient No. 1 was a 23 year old white female without current medical problems. She was on no medication and had no history of sexual problems.
2. Patient No. 2 was a 41 year old pre-menopausal white female without current medical problems. She was on no medication and had no history of sexual problems.

D. Administration

Solutions were applied directly to the clitoris by means of a calibrated micropipette (Justor 1100DG, Sigma; St. Louis, Mo.).

E. Results

The results for Patient Nos. 1 and 2 are shown in the Tables below:

Patient No. 1

|  | Temperature Change (° F.) | Change in Clitoral Blood Flow (cm/sec) | Subjective Response |
| --- | --- | --- | --- |
| PGE-2 DOSE |  |  |  |
| triacetin only | 0.4 | 0 | none |
| 0.020 mcg | 2.1 | 0 | Rare tingle. |
| 0.200 mcg | 2.4 | 11 [+50%] | Very excited. |
| 0.400 mcg | 4.5 | 12 [+92%] | Very excited, 9/10. |
| 1.000 mcg | 2.3 | 10 [+77%] | Excited, 7/10. |
| 10.0 mcg | 4.8 | 10 [+100%] | Very excited. |
| 50.0 mcg | 2.0 | 2 [+20%] | Excited. 2/10 abdominal cramping. |
| PGE-1 DOSE |  |  |  |
| Triacetin Only | 0.2 |  | None. |
| 0.400 mcg | −0.6 |  | Felt cold. |
| 1.000 mcg | 0.3 |  | Clitoral burning; 6/10; Abdominal cramping; 7/10; headache. |
| 20.0 mcg | 0.3 | 4 [+46%] | Clitoral burning; 4/10. Exciting. |
| 50.0 mcg | 0.1 | 3.5 [+32%] | Exciting. Jaw pain. |
| 100.0 mcg | 2.7 | 6.5 [+33%] | Exciting. Flushing. Pain in jaw, headache. |
| 200.0 mcg | 0.4 | 11 [+80%] | Diffuse pain, flushing, cramping. |
| R-alphamethyl-histamine Potent H3 agonist |  |  |  |
| Saline Only | −0.2 |  | None. |
| 1.0 mcg | −0.1 |  | None. |
| 10.0 mcg | −0.5 |  | Numb feeling in clitoris. |
| 100.0 mcg | 0.1 |  | Clitoral burning; 2/10; abdominal cramping, less excited than at start. |

Patient No. 2

|  | Temperature Change (° F.) | Subjective Response |
| --- | --- | --- |
| PGE-2 Dose |  |  |
| Triacetin Only | 0.2 | Felt drop go on. |
| 0.050 mcg | 1.8 | Increased sensitivity in clitoris, 5/10 general sexual stimulation. |
| 1.000 mcg | 2.4 | Excited. |
| 10.0 mcg | 2.0 | Very excited - 8/10. As good as best ever sexual excitement. |
| PGE-1 Dose |  |  |
| Triacetin Only | −0.25 | Drop felt cold. |
| 1.000 mcg | −0.35 | Felt drop go on. No excitement. |
| 10.0 mcg | −0.10 | Felt drop go on. No excitement. |
| 100.0 mcg | −0.10 | Felt nothing. |

F. Conclusions

1. Both patients showed increases in clitoral temperatures with administration of PGE-2. The increase in Patient No. 1 resulting from 0.200 mcg of PGE-2 was about equal to that produced by 100 mcg of PGE-1, indicating that PGE-2 was about 500 times more potent than PGE-1. Patient No. 2 did not have a temperature increase with PGE-1.
2. Temperature increases correlated very well with patient experiences of pleasurable sexual feelings.
3. The best dose of PGE-2 for Patient No. 1 was 0.400 mcg. Patient #1 had pleasurable feelings from PGE-1 at doses of 20 or more mcg. Patient No. 1 had adverse effects at all doses of PGE-1 and at doses of PGE-2 of 50 mcg.
4. Patient No. 2 had a sexual response from administration of PGE-2 in an amount of 0.050 mcg or greater. Patient No. 2 had neither positive nor negative effects from PGE-1.
5. R-alphamethylhistamine decreased temperature and decreased sexual excitement in Patient No. 1.

Patient No. 1 was later treated with a triacetin solution containing a PGDH inhibitor (palmitic acid) and PGE2 in a 10:1 weight ratio. The addition of palmitic acid further enhanced the potency of the PGE2 resulting in an increase in clitoral blood flow at a dose of 0.4 nanograms of PGE2 and subjective reports of a sexual response at 2 nanograms of PGE2.

Obviously, numerous modifications and variations of the present invention are possible in light of the above-given teachings. It is therefore to be understood that, within the scope of the appended claims, the invention may be practiced otherwise than as specifically described herein.

What is claimed as new and desired to be secured by Letters Patent of the United States is:

1. A method for enhancing female sexual desire and response, comprising topically administering to the clitoris of a subject a pharmaceutical composition containing an effective amount of a prostaglandin on an as-needed basis without regular dosing in the context of a chronic dosage regimen.

2. The method of claim 1, wherein said prostaglandin is selected from the group consisting of prostaglandin E-1; prostaglandin E-2; prostaglandin F-2α; prostaglandin A-1; prostaglandin B-1; prostaglandin D-2; prostaglandin E-M; prostaglandin F-M; prostaglandin H-2; prostaglandin I-2; 19-hydroxy-prostaglandin A-1; 19-hydroxy-prostaglandin B-1; prostaglandin A-2; prostaglandin B-2; 19-hydroxyprostaglandin A-2; 19-hydroxy-prostaglandin B-2; prostaglandin B-3; prostaglandin F-1α; 15-methyl-prostaglandin F-2α.; 16,16-dimethyl-α-$\Delta^2$-prostaglandin E-1 methyl ester; 15-deoxy-16-hydroxy -16-methyl-prostaglandin E-1 methyl ester; 16,16-dimethyl-prostaglandin E-2; 11-deoxy-15-methyl-prostaglandin E-1; 16-methyl-18,18,19,19-tetrahydrocarbacyclin; (16RS)-15-deoxy-16-hydroxy-16-methyl-prostaglandin E-1 methyl ester; (+)-4,5-didehydro -16-phenoxy-α-tetranor-prostaglandin E-2 methyl ester; 11-deoxy-11a, 16,16-trimethyl -prostaglandin E-2; (+)-11a,16a,b-dihydroxy-1,9-dioxo-1-(hydroxymethyl)-16-methyl -trans-prostene; 9-chloro-16,16-dimethyl-prostaglandin E-2; and arboprostil.

3. The method of claim 1, wherein said prostaglandin is selected from the group consisting of prostaglandin E-1, prostaglandin E-2, prostaglandin F-2α, prostaglandin D-2, prostaglandin F-1α, 15-methyl-prostaglandin F-2α, prostaglandin E-3, prostaglandin D-1, and misoprostol.

4. The method of claim 1, wherein said prostaglandin is applied to said clitoris in an amount of 0.1 nanograms to 2,000 µg.

5. The method of claim 1, wherein said prostaglandin is prostaglandin E-1.

6. The method of claim 1, wherein said prostaglandin is prostaglandin E-2.

7. The method of claim 1, further comprising coadministration of at least one coagent selected from the group consisting of agents which inhibit 15-hydroxyprostaglandindehydrogenase, ACE inhibitors, nitro vasodilators, alpha blockers, yohimbine, labetalol, carvedilol, bucindolol, phosphodiesterase inhibitors, muscarinic agents, dopaminergic agonists, ergot alkaloids, opiate antagonists, and polypeptide neurotransmitters.

8. The method of claim 1, wherein the prostaglandin is a unit dose.

9. The method of claim 8, wherein the unit dose is in the range of about 20 nanograms to about 2000 µg.

10. The method of claim 9, wherein the unit dose is in the range of about 200 nanograms to about 500 µg.

11. The method of claim 1, wherein the pharmaceutical composition further comprises a topical carrier that provides release of the prostaglandin from the composition within about 1 minute to about 60 minutes following administration.

12. The method of claim 11, wherein the carrier provides release of the prostaglandin from the composition within about 5 minutes to about 30 minutes following administration.

13. The method of claim 7, wherein the at least one coagent is administered with the prostaglandin.

14. The method of claim 7, wherein the at least one coagent is administered prior to administration of the prostaglandin.

15. The method of claim 7, wherein the at least one coagent is an agent which inhibits 15-hydroxyprostaglandindehydrogenase.

* * * * *